(12) United States Patent
Yi

(10) Patent No.: US 12,253,254 B1
(45) Date of Patent: Mar. 18, 2025

(54) CANDLE WARMER LAMP

(71) Applicant: Rong Yi, Zhongshan (CN)

(72) Inventor: Rong Yi, Zhongshan (CN)

( * ) Notice: Subject to any disclaimer, the term of this patent is extended or adjusted under 35 U.S.C. 154(b) by 0 days.

(21) Appl. No.: 18/675,020

(22) Filed: May 27, 2024

(51) Int. Cl.
*F21V 35/00* (2006.01)
*A61L 9/03* (2006.01)
*F21V 1/00* (2006.01)
*F21V 23/00* (2015.01)
*F21V 23/04* (2006.01)
*F21Y 113/20* (2016.01)

(52) U.S. Cl.
CPC .............. *F21V 35/003* (2013.01); *A61L 9/03* (2013.01); *F21V 1/00* (2013.01); *F21V 23/001* (2013.01); *F21V 23/04* (2013.01); *A61L 2209/11* (2013.01); *A61L 2209/12* (2013.01); *A61L 2209/135* (2013.01); *F21Y 2113/20* (2016.08)

(58) Field of Classification Search
CPC .......... F21V 35/00; F21V 35/003; F21V 1/00; F21V 23/001; F21V 23/04; A61L 9/03; A61L 2209/11; A61L 2209/12; A61L 2209/135; F21Y 2113/20; F21S 13/12; F21S 6/002
USPC ........................................................ 362/234
See application file for complete search history.

(56) References Cited

U.S. PATENT DOCUMENTS

| | | | |
|---|---|---|---|
| 7,132,084 B1 * | 11/2006 | Roumpos ................. | A61L 9/03 422/123 |
| 2023/0366527 A1 * | 11/2023 | He ......................... | F21V 23/001 |
| 2024/0066171 A1 * | 2/2024 | Yoo .......................... | A61L 9/03 |
| 2024/0173450 A1 * | 5/2024 | Gong ....................... | A61L 9/03 |

* cited by examiner

*Primary Examiner* — Laura K Tso
(74) *Attorney, Agent, or Firm* — JEEN IP LAW, LLC

(57) ABSTRACT

A candle warmer lamp is provided, which includes a seat, a connection frame, a first light-emitting component, and a second light-emitting component. The seat is provided with a bearing surface configured to carry a container accommodating an aromatherapy candle. One side of the seat away from the bearing surface is provided with an accommodation groove, the connection frame is connected to the seat. The first light-emitting component is provided in the connection frame, a light-emitting end of the first light-emitting component is faced to the bearing surface. The second light-emitting component is accommodated in the accommodation groove. Light emitted by the second light-emitting component passes through an outer circumference side of the seat. Therefore, by providing with the second light-emitting component, a bottom of the candle warmer lamp can emit light, and a user can start the first light-emitting component and/or second light-emitting component for lighting or fragrance release.

9 Claims, 6 Drawing Sheets

CANDLE WARMER LAMP

TECHNICAL FIELD

The present disclosure relates to the field of aromatherapy equipment technologies, and in particular, to an aromatherapy lamp.

BACKGROUND

Aromatherapy candle has characteristic of fresh and pleasant fragrance, which is different from a traditional candle. The aromatherapy candle belongs to a type of craft candles, with a rich and colorful appearance. It contains natural plant essential oils, releases a pleasant fragrance when burned. The aromatherapy candle has become a way to regulate the taste of life. However, the existing lighting mode of aromatherapy lamp is relatively simple and singularity, rendering it difficult to provide softer light sources according to user needs, unable to meet people's nighttime needs, or inconvenient for a user to use.

SUMMARY

The present disclosure aims to solve at least one of the technical problems existing in the prior art. Therefore, the present disclosure proposes an aromatherapy lamp that can meet a user's use needs.

The aromatherapy lamp according to an embodiment of the present disclosure includes a seat, a connection frame, a first light-emitting component, and a second light-emitting component; the seat is provided with a bearing surface configured to carry a container accommodating an aromatherapy candle, one side of the seat away from the bearing surface is provided with an accommodation groove; the connection frame is connected to the seat; the first light-emitting component is provided in the connection frame, a light-emitting end of the first light-emitting component is faced to the bearing surface; the second light-emitting component is accommodated in the accommodation groove, light emitted by the second light-emitting component passes through an outer circumference side of the seat.

According to an embodiment of the present disclosure, the aromatherapy lamp has at least the following beneficial effects:

when it is necessary to release fragrance, the container carrying the aromatherapy candle is placed on the bearing surface, and the user can start the first light-emitting component. The first light-emitting component can continuously heat the aromatherapy candle to increase its temperature, and the aromatherapy candle is melted to release fragrance. When lighting is needed, the user can start the second light-emitting component, which can emit light from the outer circumference side of the seat to illuminate an indoor space, allowing the user to use the aromatherapy lamp for lighting and/or fragrance release, meeting the user's use needs and rendering it convenient for the user to use.

According to some embodiments of the present disclosure, the second light-emitting component is configured to be a light strip, a light-emitting end of the light strip is faced to the outer circumference side of the seat, and the light strip is arranged to extend along a circumferential direction of the seat.

According to some embodiments of the present disclosure, the aromatherapy lamp further includes a power cord and a fixing member; a notch is provided on a side wall of the accommodation groove, the power cord passes through the notch and is electrically connected to the second light-emitting component; the fixing member includes a fixing part and a connection part connected to the fixing part, the connection part is connected to the seat; one end of the fixing part away from the connection part is accommodated in the notch and abuts against the power cord.

According to some embodiments of the present disclosure, the aromatherapy lamp further includes a shading element, which is provided between the connection part and a bottom wall of the accommodation groove; a reflective layer is provided on one side of the shading element close to the light strip.

According to some embodiments of the present disclosure, the fixing part is integrated with the connection part.

According to some embodiments of the present disclosure, the light strip is bonded to the seat.

According to some embodiments of the present disclosure, the seat is made of a transparent material.

According to some embodiments of the present disclosure, a plurality of anti-glare parts are provided on the outer circumference side of the seat, and the plurality of anti-glare parts are arranged to be spaced along the circumferential direction of the seat.

According to some embodiments of the present disclosure, the aromatherapy lamp further includes a control component, which is electrically connected to the second light-emitting component so as to control an operation of the second light-emitting component.

According to some embodiments of the present disclosure, the control component is configured to be a wired control module or a wireless control module.

Other aspects and advantages of the present disclosure will be partially provided in the following description, and some will become apparent from the following description, or will be learned through the practice of the present disclosure.

BRIEF DESCRIPTION OF DRAWINGS

The above and/or other aspects and advantages of the present disclosure will become apparent and easy to understand from the description of embodiments in combination with the following drawings.

Figure 1:
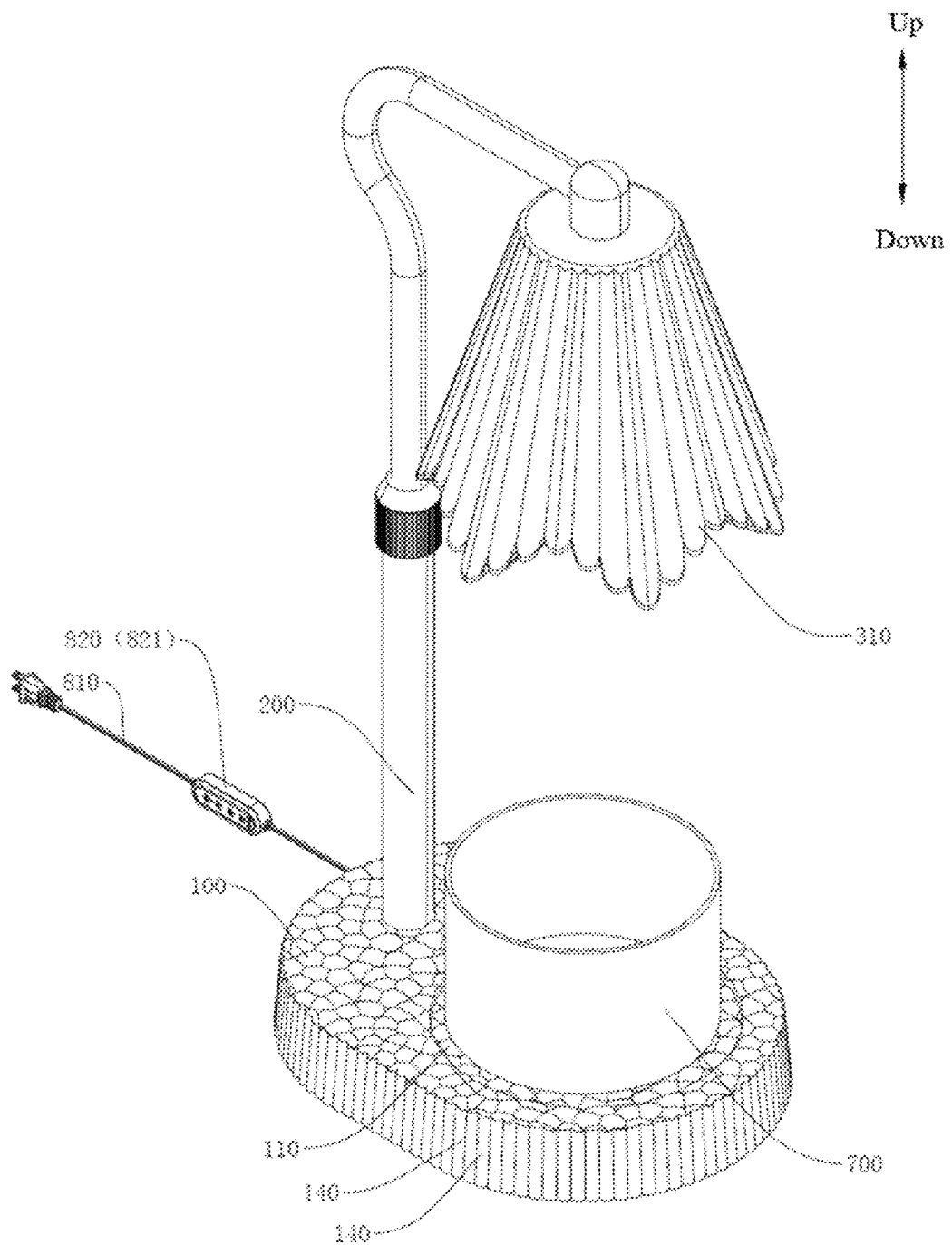
FIG. 1 is a structural schematic diagram of an aromatherapy lamp in an embodiment of the present disclosure.

Numeral reference: seat 100, bearing surface 110, accommodation groove 120, notch 130, anti-glare part 140, connection frame 200, first light-emitting component 300, lampshade 310, spotlight 320, second light-emitting component 400, fixing member 500, fixing part 510, connection part 520, shading element 600, container 700, power cord 810, control component 820, wired control module 821, wireless control module 822.

DESCRIPTION OF EMBODIMENTS

The following describes the embodiments of the present disclosure in detail, examples of which are shown in the accompanying drawings, where identical or similar labels throughout represent an identical or similar component or component with identical or similar function. The embodiments described below with reference to the accompanying drawings are illustrative and only intended to explain the present disclosure, and cannot be understood as limitations to the present disclosure.

In the description of the present disclosure, it should be understood that when it refers to a directional description, such as up, down, front, back, left, right, etc., the directional or positional relationship indicated is based on the directional or positional relationship shown in the accompanying drawings, and is only for a convenience of describing and simplifying the description of the present disclosure, rather than indicating or implying that the device or component referred to must have a specific orientation, be constructed and operated in a specific orientation. Therefore, it cannot be understood as a limitation on the present disclosure.

In the description of the present disclosure, several meanings refer to one or more, multiple meanings refer to two or more, greater than, less than, more than, etc. are understood as excluding an original number, and above, below, within, etc. are understood as including the original number. If there is a description that the first and second are only for a purpose of distinguishing technical features and cannot be understood as indicating or implying a relative importance or implying the quantity or sequence of the indicated technical feature.

In the description of the present disclosure, unless otherwise specified, words "setting", "installation", "connection", etc. should be understood in a broad sense. Those skilled in the art can reasonably determine a specific meaning of the above words in the present disclosure based on a specific content of the technical solution.

Figure 2:
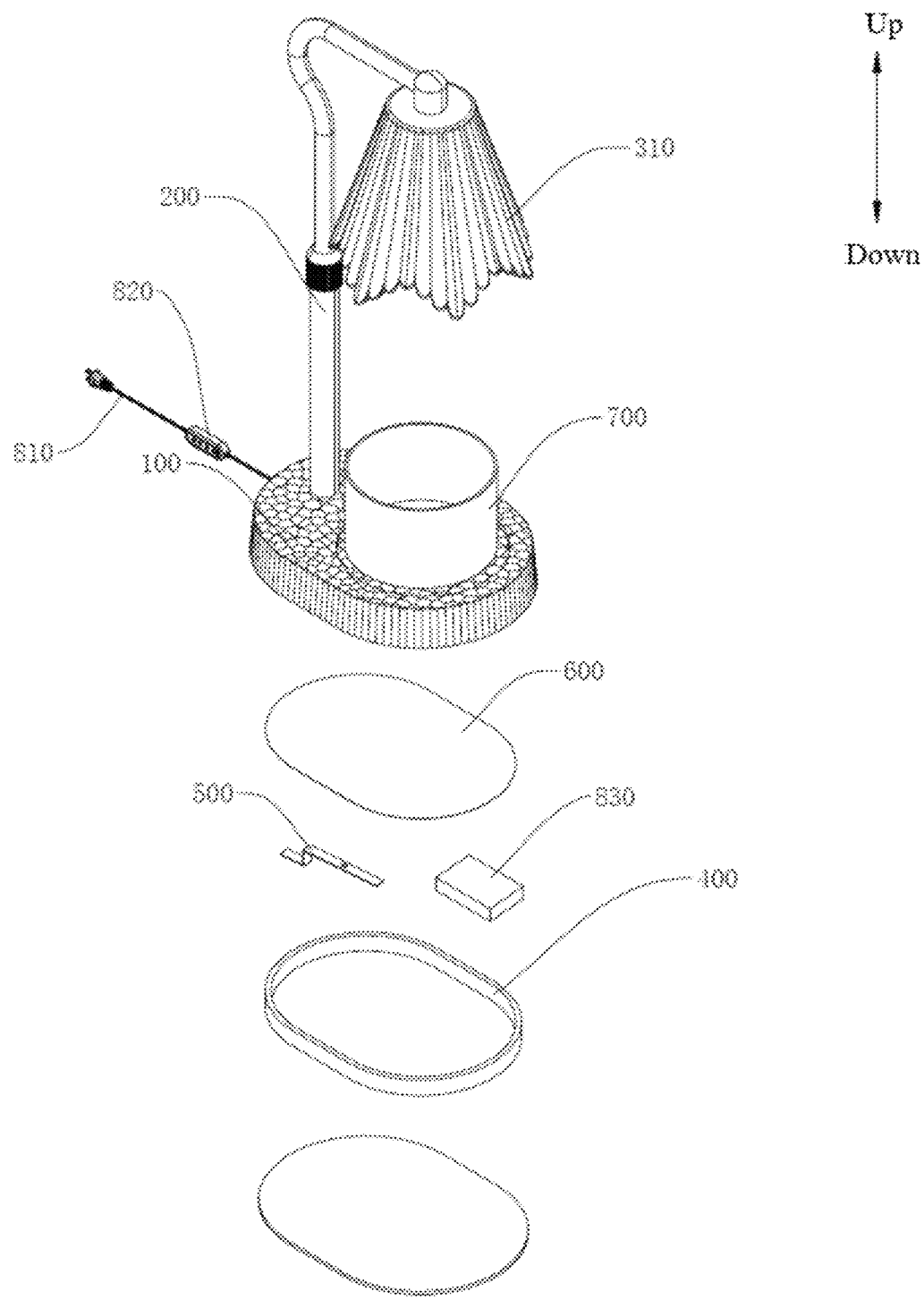
FIG. 2 is a schematic diagram of a decomposition of the aromatherapy lamp in an embodiment of the present disclosure.
Figure 3:
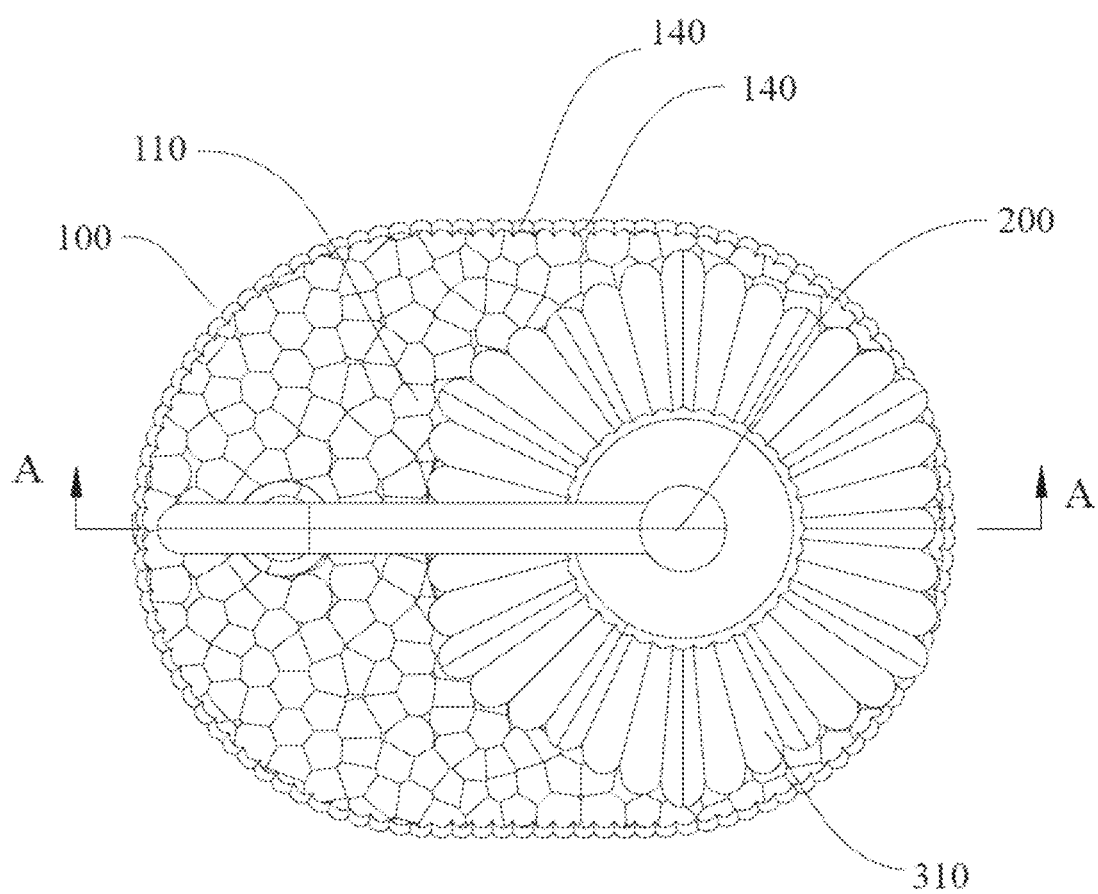
FIG. 3 is a top view of the aromatherapy lamp in an embodiment of the present disclosure.
Figure 4:
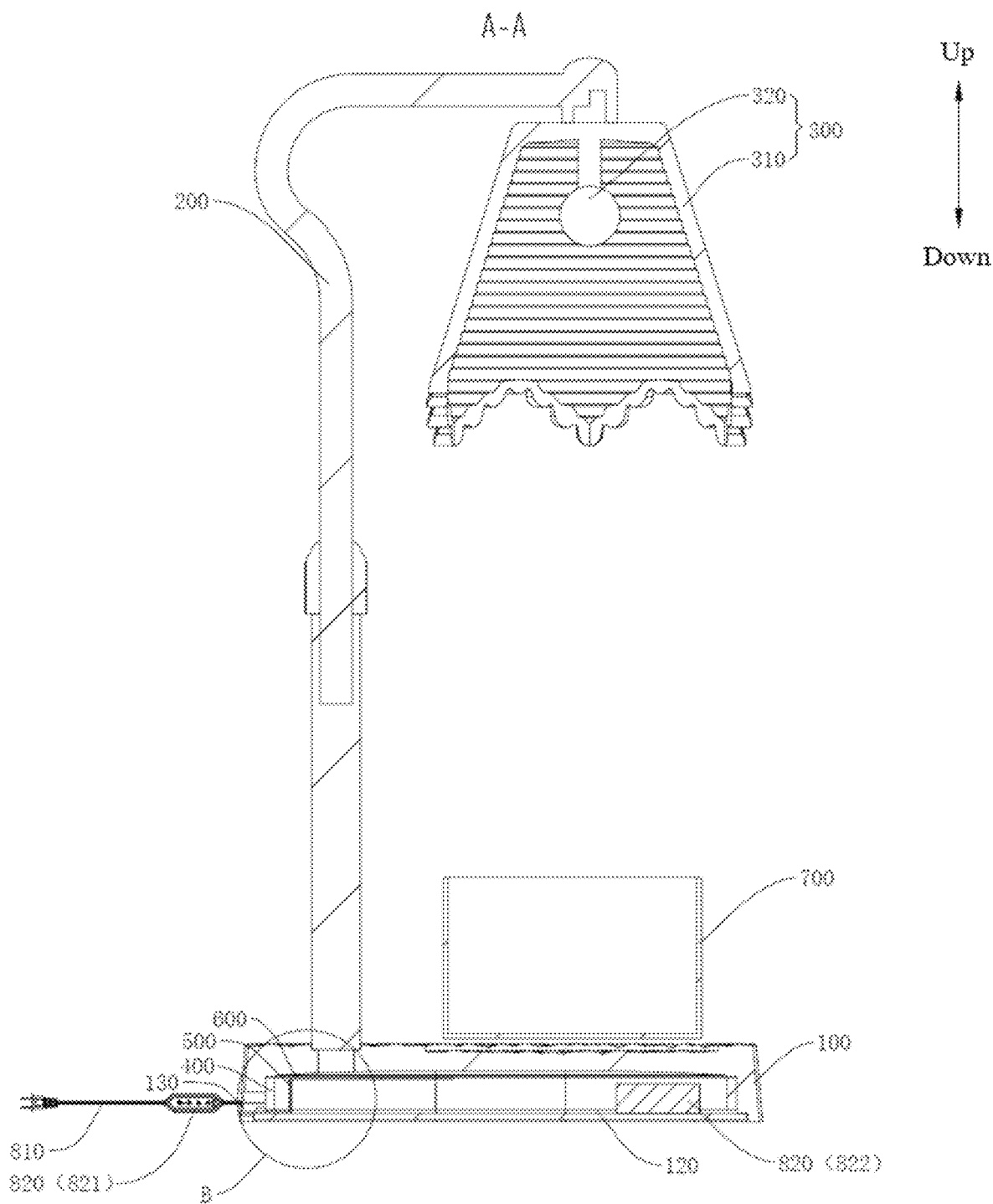
FIG. 4 is a sectional view of A-A line in FIG. 3.

Referring to FIGS. 1 and 2, the aromatherapy lamp according to an embodiment of the present disclosure includes a seat 100, a connection frame 200, a first light-emitting component 300, and a second light-emitting component 400. The seat 100 is provided with a bearing surface 110, which is configured to carry a container 700 accommodating an aromatherapy candle. One side of the seat 100 away from the bearing surface 110 is provided with an accommodation groove 120, the connection frame 200 is connected to the seat 100. The first light-emitting component 300 is provided in the connection frame 200, a light-emitting end of the first light-emitting component 300 is faced to the bearing surface 110. The second light-emitting component 400 is accommodated in the accommodation groove 120. Light emitted by the second light-emitting component 400 passes through an outer circumference side of the seat 100. Therefore, by providing with the second light-emitting component 400, a bottom of the aromatherapy lamp can emit light, allowing a user to start the first light-emitting component 300 and/or the second light-emitting component 400 for lighting and/or fragrance release, it can meet the user's need and facilitate his use.

In an implementation, when it is necessary to release fragrance, the container 700 carrying the aromatherapy candle is placed on the bearing surface 110, and the user can start the first light-emitting component 300. The first light-emitting component 300 can continuously heat the aromatherapy candle to increase its temperature, and the aromatherapy candle is melted to release fragrance. When lighting is needed, the user can start the second light-emitting component 400. The second light-emitting component 400 can emit light from the outer circumference side of the seat 100 to illuminate an indoor area, allowing the user to use the aromatherapy lamp for lighting and/or fragrance release, meeting the user's use needs and rendering it convenient for the user to us e.

It should be noted that the seat 100 can be made of a transparent material such as glass or silicone, which can facilitate the light emitted by the second light-emitting component 400 to emit light through the outer circumference side of the seat 100. This will not be elaborated here. Of course, in some specific embodiments, the seat 100 can also be made of an opaque material, and a plurality of transparent holes can be provided on a side wall of the accommodation groove 120, which will not be elaborated here.

It should be noted that the first light-emitting component 300 includes a lampshade 310 and a spotlight 320, both of which are connected to the connection frame 200, and the lampshade 310 is covered on the spotlight 320, a light-emitting end of the spotlight 320 is faced to the bearing surface 110, which can increase the temperature of the aromatherapy candle to release fragrance. This will not be elaborated here.

Referring to FIGS. 2 to 5, in some embodiments of the present disclosure, the second light-emitting component 400 is configured to be a light strip, a light-emitting end of the light strip is faced to the outer circumference side of the seat 100, and the light strip is arranged to extend along a circumference direction of the seat 100, so that the aromatherapy lamp can emit light in all directions, thereby improving the user experience, and thus increasing the market competitiveness of the product.

It should be noted that the second light-emitting component 400 can emit monochromatic or colorful light, which will not be elaborated here.

Of course, in some specific embodiments, the second light-emitting component 400 may also be a spotlight or other component, without limitation.

Figure 5:
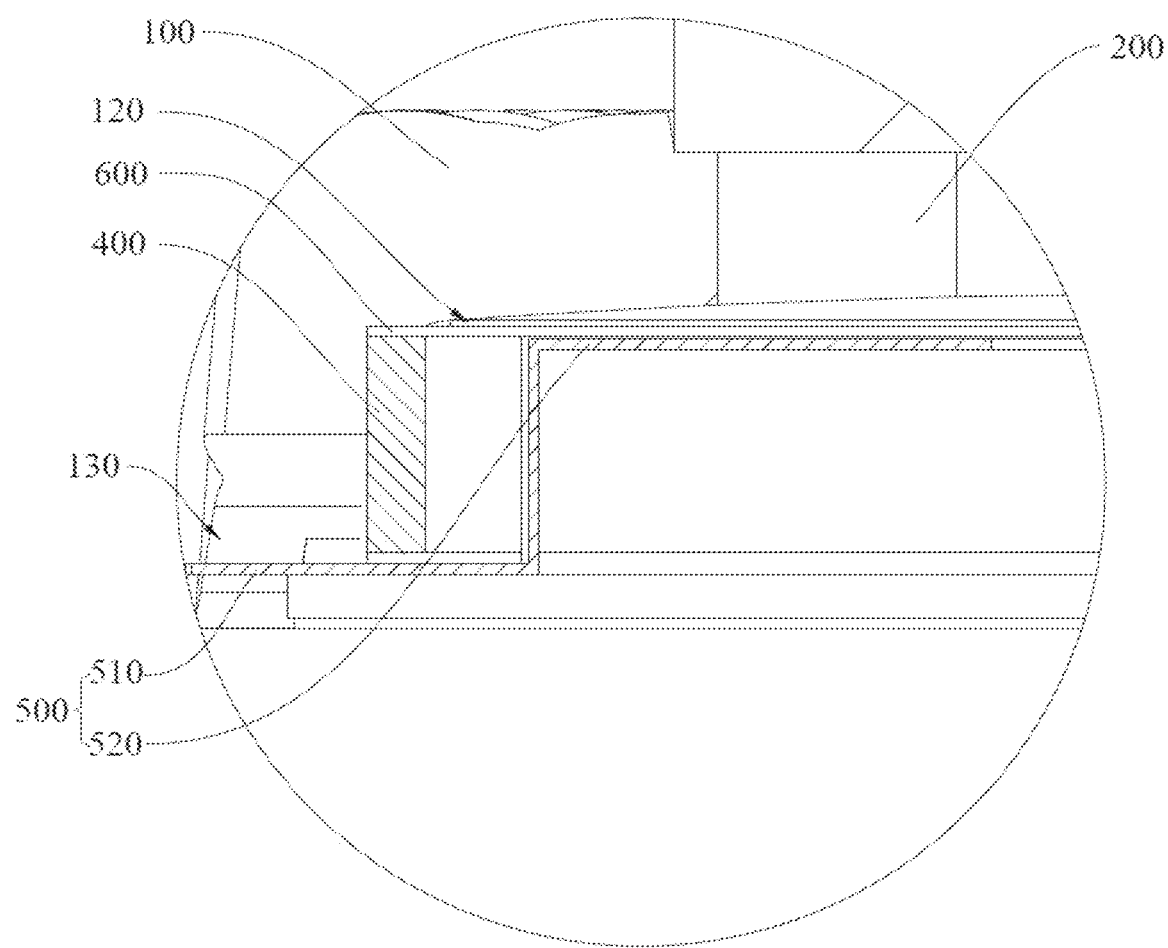
FIG. 5 is a locally enlarged view of part B in FIG. 4.
Figure 6:
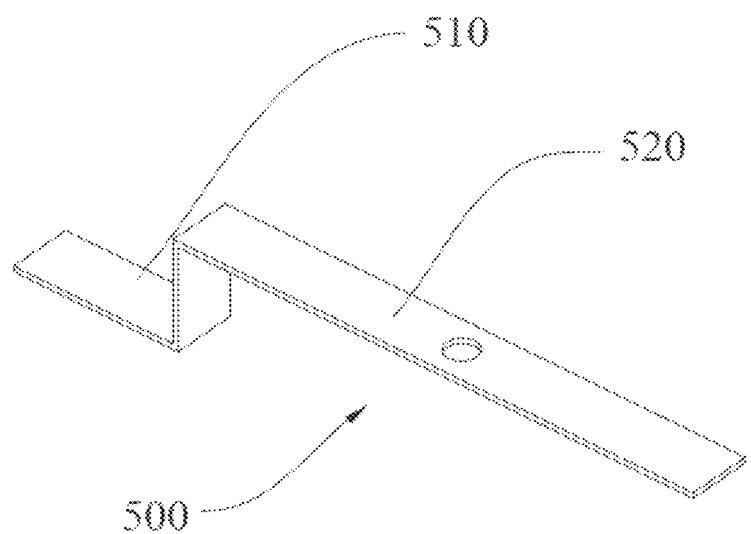
FIG. 6 is a structural schematic diagram of a fixing component in an embodiment of the present disclosure.

Referring to FIGS. 5 and 6, in some embodiments of the present disclosure, the aromatherapy lamp further includes a power cord 810 and a fixing member 500. A side wall of the accommodation groove 120 is provided with a notch 130, the power cord 810 passes through the notch 130 and is electrically connected to the second light-emitting component 400. The fixing member 500 includes a fixing part 510 and a connection part 520 connected to the fixing part 510, the connection part is connected to the seat 100. One end of the fixing part 510 away from the connection part 520 is accommodated in the notch 130 and abuts against the power cord 810, which can facilitate an assembly of the power cord 810 and improve a production efficiency of the aromatherapy lamp.

In an implementation, the notch 130 penetrates to the periphery of the accommodation groove 120, and the connection part 520 is detachably connected to a bottom wall of the accommodation groove 120 by a bolt. One end of the fixing part 510 away from the connection part 520 abuts against the power cord 810, thereby limiting the power cord 810 from shaking left and right. The power cord 810 can be fixed, which is easy to operate, convenient, fast, and can facilitate the assembly of the power cord 810 to improve the production efficiency of the aromatherapy lamp.

In some embodiments of the present disclosure, aromatherapy lamp further includes a shading element 600, which is provided between the connection part 520 and the bottom wall of the accommodation groove 120. One side of the shading element 600 close to the light strip is provided with a reflective layer, which can improve a luminous brightness of the second light-emitting component 400.

It should be noted that the shading element 600 has a sheet-like structure and is not limited here.

In some embodiments of the present disclosure, the fixing part 510 and the connection part 520 are integrated structures, which can reduce the number of molds, thereby reducing production and manufacturing costs of the aromatherapy lamp.

In an implementation, the fixing part 510 and the connection part 520 are integrated by bending, which can reduce the production cost of the aromatherapy lamp.

In some embodiments of the present disclosure, a plurality of anti-glare parts 140 are provided on the outer circumference side of the seat 100, and the plurality of anti-glare parts 140 are arranged to be spaced along the circumferential direction of the seat 100 to avoid glare generated by the second light-emitting component 400 and improve the user experience.

In an implementation, along a height direction perpendicular to the anti-glare part 140, a cross-section of the anti-glare part 140 is a semi-circular or prismatic structure, which can avoid glare generated by the second light-emitting component 400 and improve the user experience.

In some embodiments of the present disclosure, the aromatherapy lamp further includes a control component 820, which is electrically connected to the second light-emitting component 400. The control component 820 is configured to be a wired control module 821 or a wireless control module 822 to control an operation of the second light-emitting component 400, rendering it convenient for the user to use.

It should be noted that when the control component 820 is configured to be the wired control module 821, the control component 820 can be a button type control switch or a slider type control switch. When the control component 820 is configured to be the wireless control module 822, the control component 820 can be a Bluetooth connection module, which will not be elaborated here.

The various technical features of the above embodiments can be combined in any way. To render the description concise, all possible combinations of the various technical features in the embodiments have not been described. However, as long as there is no contradiction in the combination of these technical features, they should be considered within the scope of the present specification.

The above detailed explanation of the embodiment is provided in combination with the accompanying drawings, but the present disclosure is not limited to the embodiments. Within the scope of knowledge possessed by ordinary technical personnel in the technical field, various changes can be made without departing from the present application.

What is claimed is:

1. An aromatherapy lamp, comprising:
    a seat, which is provided with a bearing surface configured to carry a container accommodating an aromatherapy candle, one side of the seat away from the bearing surface is provided with an accommodation groove;
    a connection frame, which is connected to the seat;
    a first light-emitting component, which is provided in the connection frame, a light-emitting end of the first light-emitting component is faced to the bearing surface;
    a second light-emitting component, which is accommodated in the accommodation groove, light emitted by the second light-emitting component passes through an outer circumference side of the seat;
    wherein a plurality of anti-glare parts are provided on the outer circumference side of the seat, and the plurality of anti-glare parts are arranged to be spaced along a circumference direction of the seat.

2. The aromatherapy lamp according to claim 1, wherein the second light-emitting component is configured to be a light strip, a light-emitting end of the light strip is faced to the outer circumference side of the seat, and the light strip is arranged to extend along the circumference direction of the seat.

3. The aromatherapy lamp according to claim 2, further comprises a power cord and a fixing member, wherein a notch is provided on a side wall of the accommodation groove, the power cord passes through the notch and is electrically connected to the second light-emitting component;
    the fixing member comprises a fixing part and a connection part connected to the fixing part; the connection part is connected to the seat;
    one end of the fixing part away from the connection part is accommodated in the notch and abuts against the power cord.

4. The aromatherapy lamp according to claim 3, further comprises a shading element, wherein the shading element is provided between the connection part and a bottom wall of the accommodation groove, and a reflective layer is provided on one side of the shading element close to the lamp light strip.

5. The aromatherapy lamp according to claim 3, wherein the fixing part is integrated with the connection part.

6. The aromatherapy lamp according to claim 2, wherein the light strip is bonded to the seat.

7. The aromatherapy lamp according to claim 1, wherein the seat is made of a transparent material.

8. The aromatherapy lamp according to claim 1, further comprises a control component, which is electrically connected to the second light-emitting component so as to control an operation of the second light-emitting component.

9. The aromatherapy lamp according to claim 8, wherein the control component is configured to be a wired control module or a wireless control module.

* * * * *